United States Patent [19]

Mukaiyama et al.

[11] Patent Number: 5,756,790
[45] Date of Patent: May 26, 1998

[54] OPTICALLY ACTIVE COBALT (II) COMPLEXES AND METHOD FOR THE PREPARATION OF OPTICALLY ACTIVE ALCOHOLS

[75] Inventors: Teruaki Mukaiyama, Tokyo; Kiyotaka Yorozu, Kuga-gun; Takushi Nagata, Sodegaura; Toru Yamada, Sodegaura; Kiyoaki Sugi, Sodegaura, all of Japan

[73] Assignee: Mitsui Petrochemical Industries, Ltd., Tokyo, Japan

[21] Appl. No.: 722,561

[22] Filed: Sep. 27, 1996

[30] Foreign Application Priority Data

Sep. 29, 1995 [JP] Japan ................................ 7-253477

[51] Int. Cl.$^6$ .................... C07F 15/06; C07F 7/00; C07C 29/14
[52] U.S. Cl. .................... 556/32; 556/42; 556/45; 556/51; 556/130; 556/136; 556/146; 568/880; 568/885
[58] Field of Search .................... 556/32, 42, 45, 556/51, 130, 136, 146; 568/880, 885

[56] References Cited

PUBLICATIONS

Massonneau et al., Journal Of Organometallic Chemistry, vol. 288, pp. C59–C60 (1985).

*Primary Examiner*—Porfirio Nazario-Gonzalez
*Attorney, Agent, or Firm*—Sherman and Shalloway

[57] ABSTRACT

The invention provides a method for preparing an optically active alcohol comprising the step of reacting a ketone compound with a hydride reagent in the presence of an optically active metal compound. The resulting optically active alcohols are useful as intermediates for the synthesis of physiologically active compounds such as drugs and pesticides, functional materials such as liquid crystals, and raw materials for synthesis in fine chemistry. A novel optically active cobalt (II) complex useful as a catalyst is also provided.

27 Claims, 2 Drawing Sheets

OPTICALLY ACTIVE COBALT (II) COMPLEXES AND METHOD FOR THE PREPARATION OF OPTICALLY ACTIVE ALCOHOLS

BACKGROUND OF THE INVENTION

1. Field of the Invention

This invention relates to a method for preparing optically active alcohols as well as novel optically active metal complexes (cobalt (II) complexes). More particularly, it relates to a method for preparing optically active alcohols useful as intermediates for the synthesis of physiologically active compounds such as drugs and pesticides, functional materials such as liquid crystals, and raw materials for synthesis in fine chemistry. It also relates to novel optically active metal complexes which are useful as a catalyst in the inventive method.

2. Description of the Related Art

As a general rule, alcohols are synthesized from corresponding ketones. A variety of methods are known for the synthesis of alcohols. For the preparation of optically active alcohols from ketones, there are known several methods including (1) utilization of enzymes and (2) utilization of chemical reaction. The enzyme utilizing method (1) typically uses baker's yeast (*Saccharomyces cerevisiae*) to prepare optically active alcohols from ketones. With regard to the reduction of ketones with baker's yeast, it is generally believed that a hydride attacks a carbonyl group at its re plane to produce a S isomer of optically active secondary alcohol in accordance with Prelog rule. This method, however, suffers from the problems that selectivity largely depends on the substrate and that only one of two enantiomers can be synthesized. Known as the chemical reaction utilizing method (2) is hydrogenation using a BINAP ruthenium complex. This method has the problems that reaction must be done in a hydrogen atmosphere under a pressure as high as 20–100 atm. and preparation of a catalyst is cumbersome.

On the other hand, there is known a hydride reducing method of reducing a ketone using an optically active metal hydride in the form of a metal hydride (as typified by aluminum hydride and sodium boron hydride or diborane) modified with an optically active protonic compound. This hydride reducing method, however, needs more than an equivalent of the optically active protonic compound. Izuno, Corey, et al. recently proposed a catalytic asymmetric hydride reducing method using an aminoalcohol derived from naturally occurring L-proline and a boran-sulfide complex. Improvements in handling and cost are desired for this method because the boran-sulfide complex is used as a reducing agent.

SUMMARY OF THE INVENTION

Therefore, an object of the present invention is to provide a method for preparing an optically active alcohol using a hydride reducing agent which is easy to handle. The resulting optically active alcohol are useful as intermediates for the synthesis of physiologically active compounds such as drugs and pesticides, functional materials such as liquid crystals, and raw materials for synthesis in fine chemistry.

Another object of the present invention is to provide a novel optically active metal complex such as active cobalt complexes which is useful as a catalyst in the method for preparing an optically active alcohol.

Making efforts to develop a method capable of synthesizing optically active alcohols from ketones using easy-to-handle hydride reagents as a reducing agent, we have found that the above-mentioned object can be attained by catalyzing reaction with an optically active metal compound.

Making efforts to have an optically active metal compound which is effective as a catalyst in the preparation of optically active alcohols, we have found a "novel optically active metal complex" such as an optically active cobalt complex.

Briefly stated, the present invention provides a method for preparing an optically active alcohol by reacting a ketone compound with a hydride reagent in the presence of an optically active metal compound.

Further, the present invention provides a method for preparing an optically active alcohol from a ketone compound with a hydride reagent in the presence of an optically active metal compound along with an alcohol compound. Preferably, the optically active metal compound used as a catalyst in the inventive method is an optically active cobalt (II) complex. More specifically, the optically active cobalt (II) complex is of the following general formula (a):

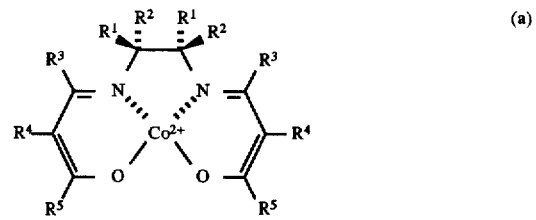

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent.

In another aspect, the present invention provides a novel optically active metal (II) complex of the general formula (a').

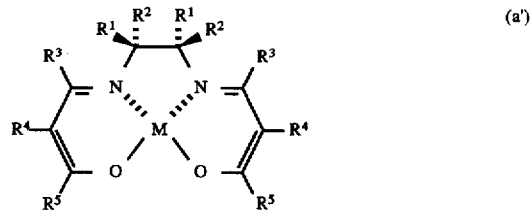

wherein $R^1$, $R^2$, $R^3$, $R^4$ and $R^5$ are the same as in the formula (a) and M is an optically active transition metal compound discussed below.

DETAILED DESCRIPTION OF THE INVENTION

Figure 1:
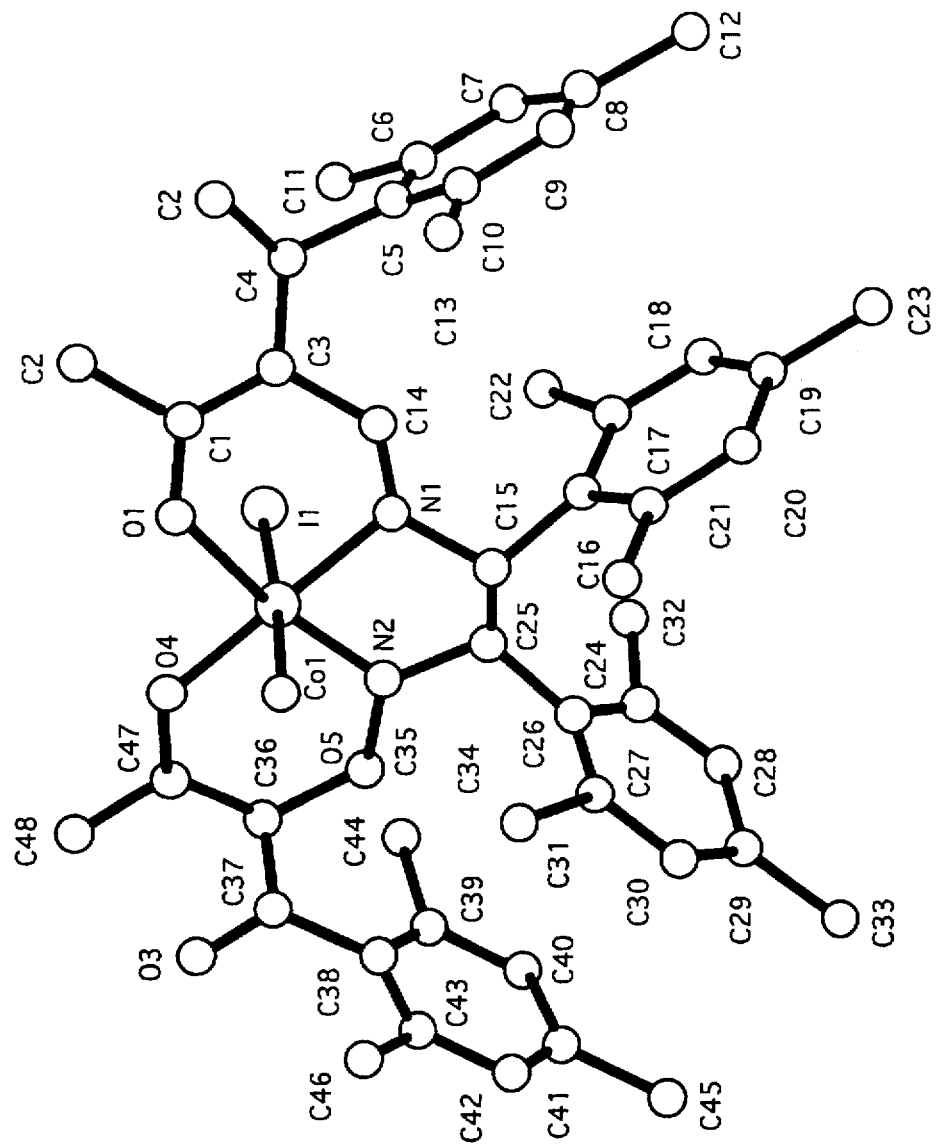
FIG. 1 illustrates the structure as determined by X-ray diffractometry of an optically active cobalt (II) complex of formula (a-18) prepared in Example 66.
Figure 2:
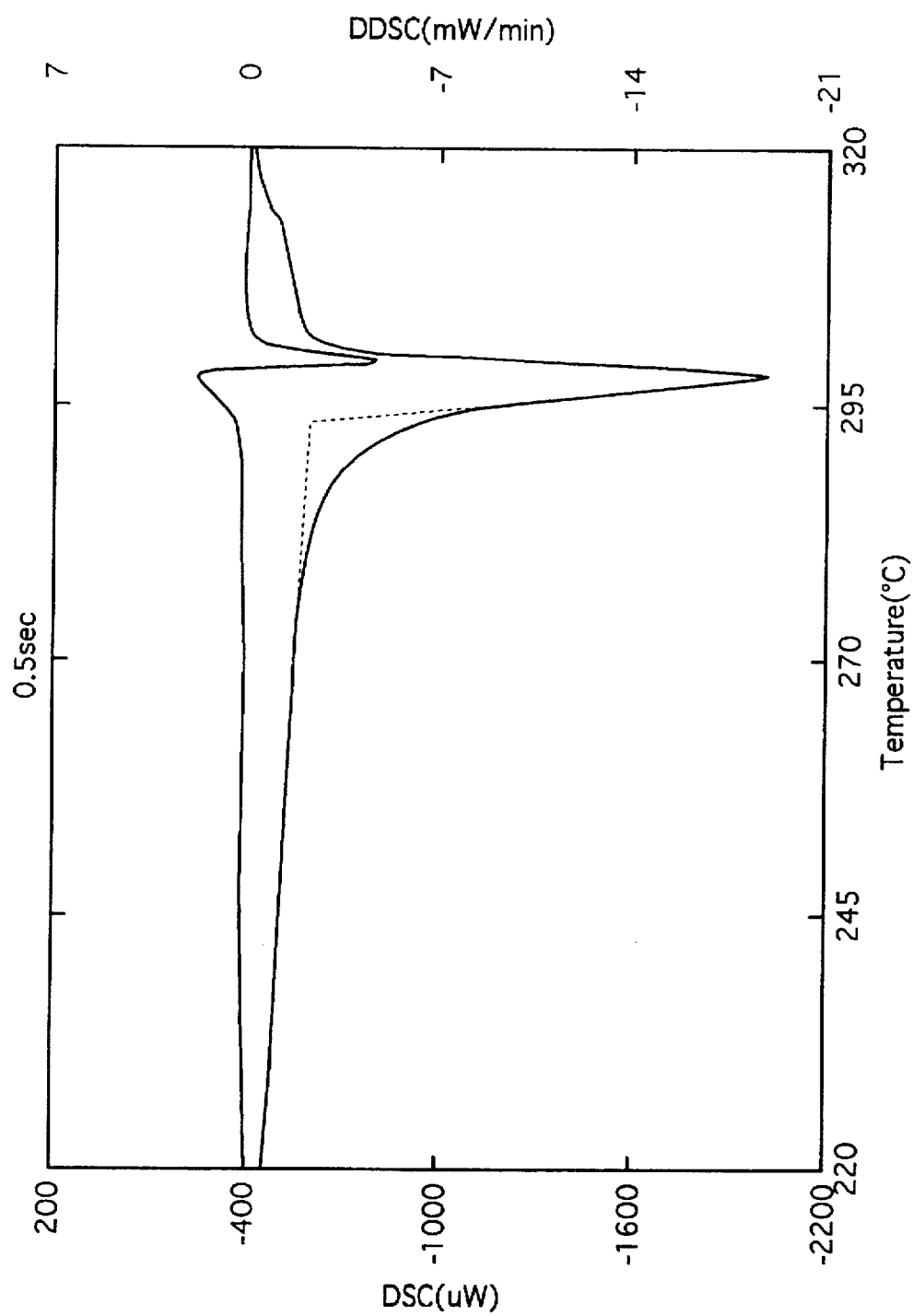
FIG. 2 diagrammatically illustrates a differential scanning calorimetry curve of an optically active cobalt (II) complex of formula (a-7) prepared in Example 67.

The method for preparing an optically active alcohol according to the invention, referred to as an "inventive method." and the novel optically active cobalt (II) complex are described in detail.

The inventive method starts with a ketone compound which is not critical insofar as it is a prochiral compound having a carbonyl group in a molecule. Any desired ketone compound may be selected in accordance with an end optically active alcohol.

Better results are obtained from the inventive method when a ketone compound of the following general formula (b) is used as a starting material to produce a corresponding optically active alcohol.

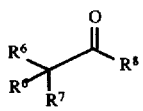
(b)

In formula (b), each of $R^6$, $R^7$, and $R^8$ is a normal or branched alkyl group, cycloalkyl group or aromatic group, which may have a substituent. Typical examples of the normal or branched alkyl group represented by $R^6$, $R^7$, and $R^8$ include methyl, ethyl, n-propyl, and n-butyl groups. Cyclohexyl is a typical example of the cycloalkyl group. Typical examples of the aromatic group include aryl groups such as phenyl, p-methoxyphenyl, p-chlorophenyl, p-fluorophenyl, α-naphthyl, and β-naphthyl groups; and heterocyclic aromatic groups such as furan, thiophene, and pyridine rings. Alternatively, two $R^6$ groups, taken together, may form a ring, or $R^7$ and $R^8$, taken together, may form a ring.

Typical examples of the ketone compound used as the starting material in the inventive method are aromatic ketones such as α-tetralone, acetophenone, and 2,2-dimethylchromanone.

The inventive method is most effective when a fused ring type ketone as typified by an acetophenone derivative of the following formula (b-1), an alpha(α)-tetralone derivative of the following formula (b-2) or a chromanone of the following formula (b-3) is used as the starting material to produce a corresponding alcohol.

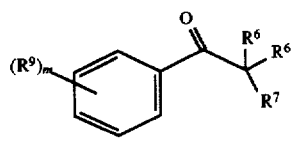
(b-1)

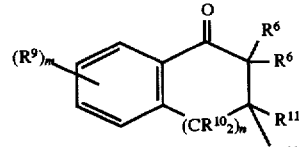
(b-2)

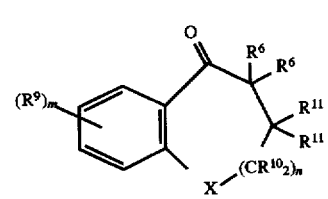
(b-3)

In these formulae, $R^6$ and $R^7$ are as defined in formula (b).

Each of $R^9$, $R^{10}$, and $R^{11}$, which may be the same or different, is a hydrogen atom, halogen atom, normal or branched alkyl, cycloalkyl, aryl, nitro, cyano, alkoxy, acyl, alkoxycarbonyl, amino or silyl group, which may have a substituent. Typical examples of the halogen atom include fluorine, chlorine and bromine. Typical examples of the normal or branched alkyl group include methyl, ethyl, isopropyl, n-propyl, t-butyl, sec-butyl, and n-butyl groups. Cyclohexyl group is a typical example of the cycloalkyl group. Typical examples of the aryl group include phenyl, p-methoxyphenyl, p-chlorophenyl, p-fluorophenyl, and naphthyl groups. Benzyloxy group is a typical example of the alkoxy group. Typical examples of the acyl group include acetyl and propionyl groups. Typical examples of the alkoxycarbonyl group include methoxycarbonyl, ethoxycarbonyl, n-butoxycarbonyl, n-octyloxycarbonyl, and benzyloxycarbonyl groups. Typical examples of the amino group include dimethylamino and diethylamino groups. Typical examples of the silyl group include trimethylsilyl and t-butyldimethylsilyl group. Letter n is equal to 0 or 1, and m is an integer of 1 to 4. When m is an integer of 2 to 4, a corresponding plurality of $R^9$ groups may be the same or different. Alternatively, two $R^{10}$ groups, taken together, may form a ring, or two $R^{11}$ groups, taken together, may form a ring. For example, the $R^{10}$ or $R^{11}$ groups are joined together through a linkage such as —$(CH_2)_4$— and —$(CH_2)_5$— to form a spiro ring structure such as five- and six-membered rings.

X is a hetero-atom such as oxygen, nitrogen and sulfur.

When an acetophenone derivative of formula (b-1), an α-tetralone derivative of formula (b-2) or a chromanone of formula (b-3) is used as the starting ketone compound, a corresponding optically active alcohol of the following general formula (c-1), (c-2) or (c-3) is obtained.

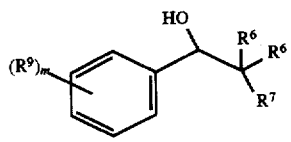
(c-1)

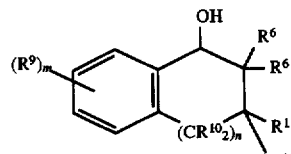
(c-2)

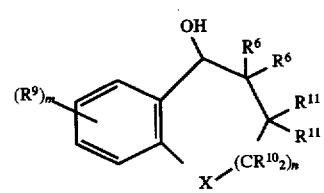
(c-3)

In these formulae, $R^6$ to $R^{11}$, n and m are as defined above.

Examples of the optically active alcohol of formula (c-1), (c-2) or (c-3) include phenethyl alcohol, α-tetralol, 2,2-dimethyl-1-tetralol, 2,2-dimethylchromanol, and 7-ethoxycarbonylchromanol.

In the inventive method, an optically active (m) compound is used as a catalyst. The optically active metal compound is not particularly limited and is typically a complex of at least one transition metal selected from the group consisting of titanium, vanadium, manganese, iron, cobalt, zinc, nickel, ruthenium, rhodium, hafnium, and zirconium. Preferably the transition metal complex is an optically active titanium (IV) complex, optically active iron (III) complex, optically active ruthenium (III) complex, optically active oxovanadium (IV) complex, optically active manganese (III) complex, optically active cobalt (III) complex or optically active cobalt (II) complex.

In the practice of the invention, an optically active alcohol is obtained in high optical yields particularly when an optically active cobalt (II) complex of the following general formula (a) is used. This optically active cobalt (II) complex of formula (a) is novel.

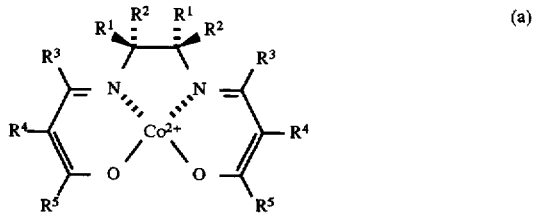

(a)

In formula (a), $R^1$ and $R^2$ are different. Each of $R^1$ and $R^2$ is a hydrogen atom, normal or branched alkyl group or aryl group, which may have a substituent. Typical examples of the normal or branched alkyl group include methyl, ethyl, isopropyl, n-propyl, t-butyl, sec-butyl, and n-butyl groups. Typical examples of the aryl group include phenyl, p-methoxyphenyl, p-chlorophenyl, p-fluorophenyl, and naphthyl groups. Alternatively, two $R^1$ groups, taken together, may form a ring, or two $R^2$ groups, taken together, may form a ring. For example, the two $R^1$ or $R^2$ groups are joined together through a linkage such as —$(CH_2)_4$— to form a ring structure such as a six-membered ring.

$R^3$, $R^4$ and $R^5$ may be the same or different. Each of $R^3$, $R^4$ and $R^5$ is a hydrogen atom, normal or branched alkyl group, aryl group, acyl group or alkoxycarbonyl group, which may have a substituent. Typical examples of the normal or branched alkyl group include methyl, ethyl, isopropyl, n-propyl, t-butyl, sec-butyl, and n-butyl groups. Typical examples of the aryl group include phenyl, p-methoxyphenyl, p-chlorophenyl, p-fluorophenyl, and naphthyl groups. Typical of the acyl group are acetyl, perfluoroacetyl, propionyl, butyryl, isobutyryl, and pivaloyl groups. Typical of the alkoxycarbonyl group are methoxycarbonyl, cyclopentyloxycarbonyl, cyclohexyloxycarbonyl, cyclooctyloxycarbonyl, and benzyloxycarbonyl groups.

Illustrative examples of the optically active cobalt (II) complex of formula (a) include those of the following formulae (a-1) through (a-17).

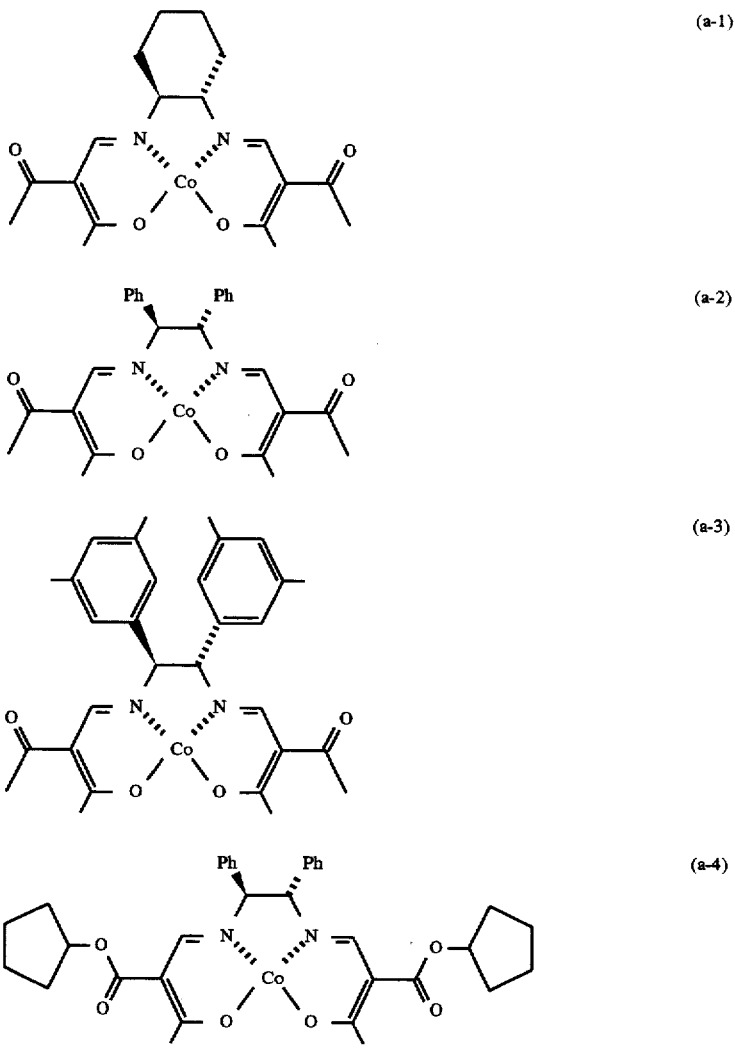

-continued
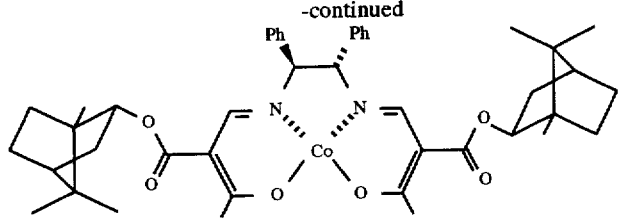
(a-5)
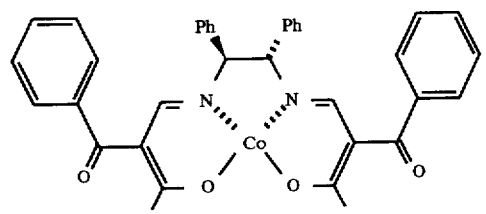
(a-6)
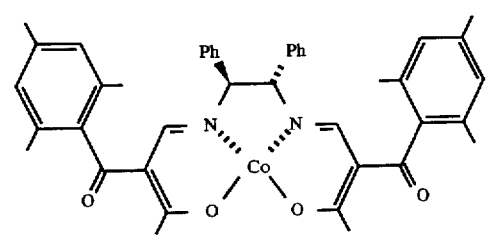
(a-7)
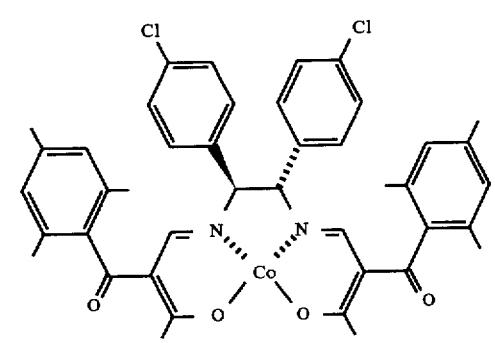
(a-8)
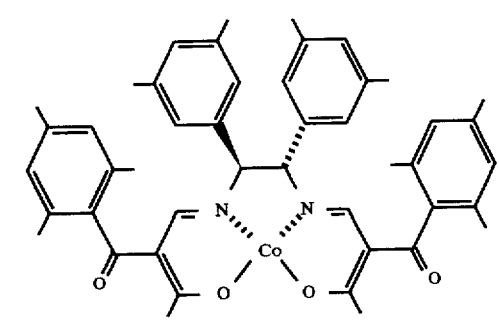
(a-9)
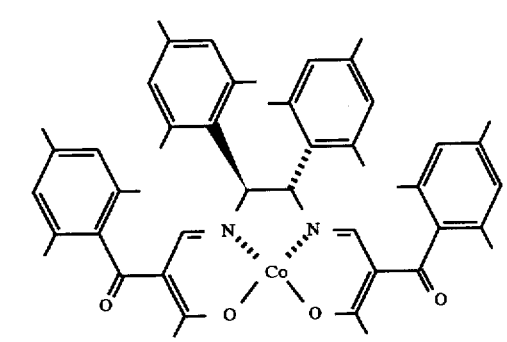
(a-10)

-continued
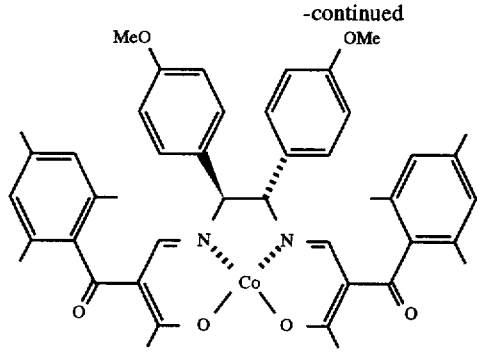
(a-11)
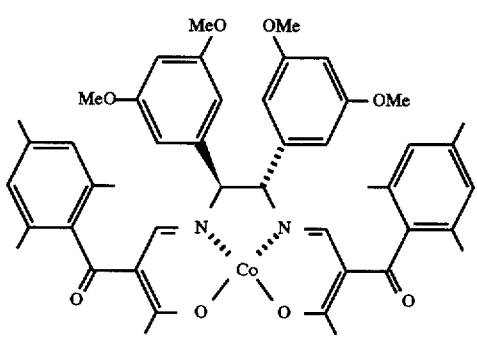
(a-12)
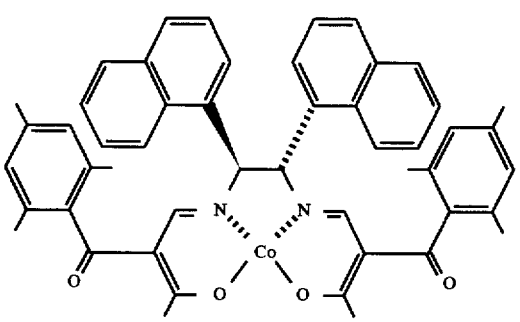
(a-13)
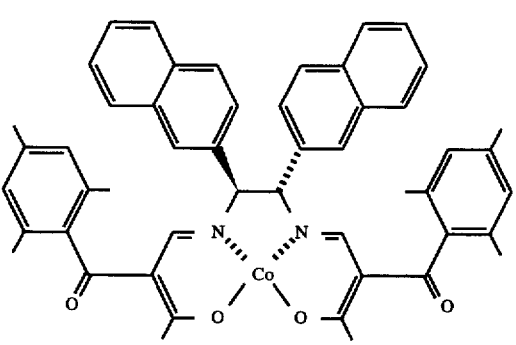
(a-14)
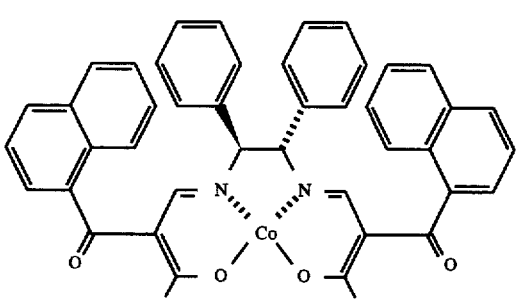
(a-15)

-continued

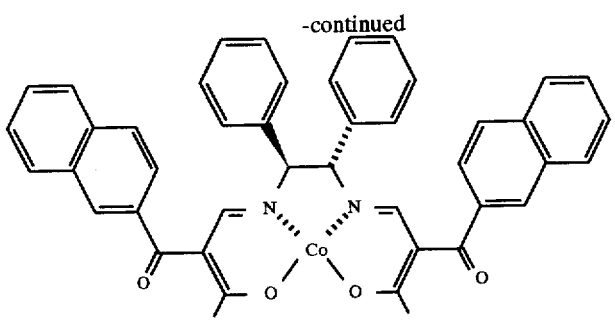

(a-16)

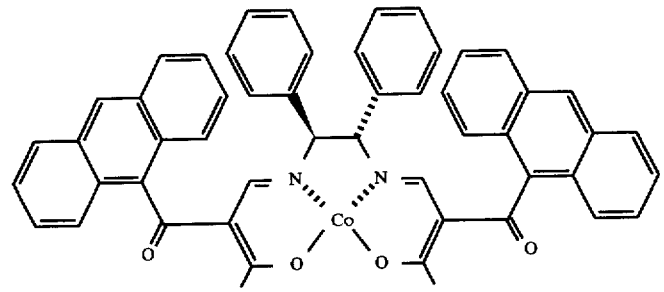

(a-17)

This novel optically active cobalt (II) complex of formula (a) can be prepared by well-known methods. For example, it can be prepared by the methods reported in Y. Nishida et al., Inorg. Chim. Acta. 38, 213 (1980); L. Claisen, Ann. Chem., 297, 57 (1987); and E. G. Jager, Z. Chem., 8, 30, 392 and 475 (1968). More illustratively, an optically active cobalt (II) complex can be prepared by formylating a 1,3-diketone derivative, being carried out dehydration and condensation reaction with a 1,2-diphenyldiamine derivative for inducing asymmetry to form a ligand, adding an aoueous solution of cobalt (II) chloride, and heating the mixture in the presence of sodium hydroxide. For example, an optically active cobalt (II) complex of formula (a-7) can be prepared through steps (e-1) and (e-2) shown below.

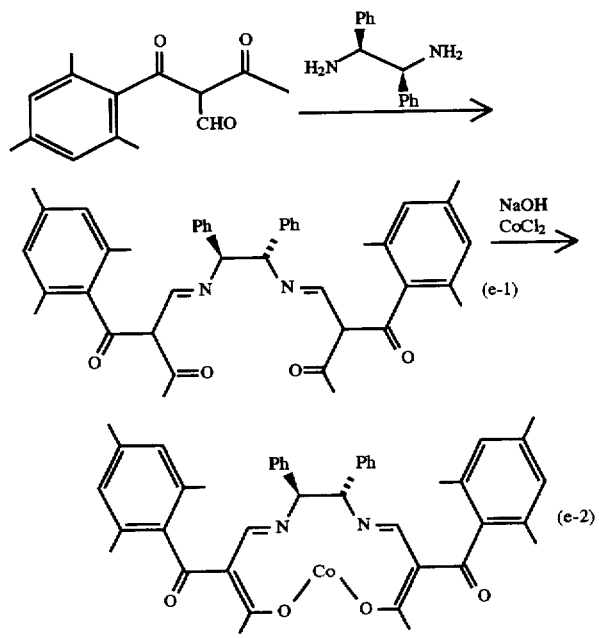

In the preparation of the optically active cobalt (II) complex, formulation of a 1,3-diketone derivative may be carried out, for example, by adding 1–5 molar equivalent of trimethyl orthoformate, and heating under reflux in a solution of acetic anhydride.

It may be carried out the dehydration and condensation reaction with optically active diamine by adding 2 equivalent amount of the above fiormylation product, which is stirred for 2 hours at room temperature, and then heated to 50° C.

A crude product obtained by thickening of the mixture may be purified by general process such as silica gel column chromatography, reprecipitation and recrystallation.

The amount of sodium hydroxide used in the reaction forming the complex of the ligand and cobalt (II) chloride is more than 2.0 molar equivalent, preferably 2.0–3.0 molar equivalent per of the ligand.

The aqueous solution of cobalt (II) chloride is used in an a-mount of more than 1.0 molar equivalent, preferably 1.0–1.5 molar equivalent of the cobalt (II) chloride per of the ligand.

The reaction is carried out in the flow of nitrogen or argon gas and solvent and water is used in deaerated. Though the reaction can be progressed even at 0° C., the reaction time can be shortened by heating generally to 30°–80° C. The heating temperature is preferably 40°–60° C.

Prefered solvent used herein include alcohol solvents such as methanol, ethanol, 2-propanol or the like.

In the preparation of the optically active cobalt (II) complex, after adding the solution of cobalt (II) chloride the optically active cobalt (II) complex may begin to deposite in 1–10 minutes, and then heating and stirring is run for additional 30 minutes to 2 hours. The reaction product is fully deposited by adding water if necessary. In nitrogen gas, the reaction product is filtered and washed with water, and the object can be then obtained by drying in a vacuum.

In the present invention, obtained optically active cobalt (II) complex is likely to be oxidized in air that a structural analysis of the optically active cobalt (II) complex may be carried out after converted to a cobalt (III) complex which is stable in air. That is, 0.5 molar equivalent of iodine(I2) is added to the optically active cobalt (II) and the mixture is stirred. Resulting product is concentrated and recrystallized in dichloromethane- diethylether-hexane mixtue to obtain a crystal of cobalt (III) complex. The obtained crystal of the cobalt (III) complex can be analyzed by X-ray diffractometry. For example, an optically active cobalt (II) complex of formula (a-10) must be converted into an optically active cobalt (III) complex of formula (a-18) shown below before structural analysis can be carried out by X-ray diffractometry. This optically active cobalt (III) complex of formula (a-18) is also useful as a catalyst in the inventive method.

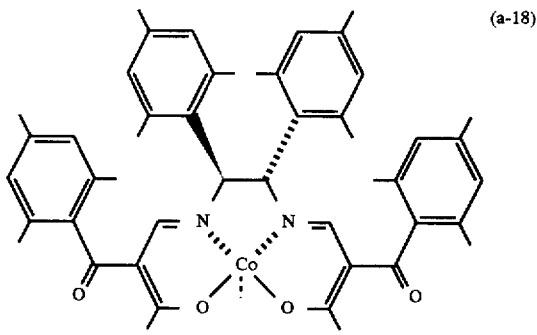

(a-18)

When an optically active cobalt (II) complex of formula (a) is used as the catalyst in the inventive method, it is desirable to use the optically active cobalt (II) complex in a proportion of 0.001 to 50 mol %, more preferably 0.01 to 50 mol %, most preferably 0.05 to 10 mol % per mol of the ketone compound in order that an optically active alcohol be produced in high optical and chemical yields.

Although the inventive method is basically by reacting a ketone compound with a hydride reagent in the presence of an optically active metal compound as typified by an optically active cobalt (II) complex of formula (a), it is preferred to carry out the reaction in the co-presence of an alcohol compound.

The alcohol compound used herein is typically of the following formula (d).

(d)

In formula (d), $R^{12}$, $R^{13}$, and $R^{14}$ may be the same or different. Each of $R^{12}$, $R^{13}$, and $R^{14}$ is a hydrogen atom, normal or branched alkyl group, cycloalkyl group, aryl group or normal or branched ether group containing a hetero-atom, which may have a substituent such as hydroxyl, amino, ester and carbonyl groups. Typical examples of the normal or branched alkyl group include methyl, ethyl, isopropyl, n-propyl, t-butyl, sec-butyl, and n-butyl groups. Typical examples of the cycloalkyl group include cyclopentyl, cyclohexyl, and cycloheptyl groups. Typical examples of the aryl group include phenyl, p-methoxyphenyl, p-chlorophenyl, p-fluorophenyl, and naphthyl groups. Typical of the normal or branched ether group containing a hetero-atom are methoxyethyl, methoxypropyl, 2-furyl, 3-furyl, and 2-tetrahydropyranyl groups. Alternatively, $R^{12}$ and $R^{13}$, taken together, may form a ring. For example, these groups are joined together through a linkage such as —$(CH_2)_4$— and —$(CH_2)_5$— to form a ring such as five- and six-membered rings.

Examples of the alcohol compound include aliphatic or alicyclic alcohols such as methanol, ethanol, propanol, isopropanol, butanol, sec-butanol, t-butanol, cyclopentanol, cyclohexanol, and cycloheptanol; aromatic alcohols such as phenol and resorcin; polyalcohols such as ethylene glycol and propylene glycol; chain-like or cyclic ether alcohols such as ethylene glycol monomethyl ether, ethylene glycol monoethyl ether, propylene glycol monomethyl ether, tetrahydrofurfuryl alcohol, tetrahydropyrane-2-methanol, furfuryl alcohol, and tetrahydro-3-furan-methanol; and chain-like and cyclic aminoalcohols such as 2-(methylamino) ethanol, 2-(ethylamino)ethanol, 2-pyridinemethanol, and 2-piperidinemethanol. Among others, aliphatic alcohols are preferred because optically active alcohols are obtained in high optical and chemical yields.

In the practice of the invention, the alcohol compounds of formula (d) may be used alone or in admixture of two or more. Exemplary combinations of two or more alcohol compounds are ethanol/ethylene glycol, ethanol/propylene glycol, ethanol/ethylene glycol monomethyl ether, ethanol/ propylene glycol monomethyl ether, ethanol/ tetrahydrofurfuryl alcohol, ethanol/tetrahydropyrane-2-methanol, ethanol/furfuryl alcohol, ethanol/tetrahydro-3-furan-methanol, and ethanol/5-methyltetrahydrofuran-2-methanol. Also useful are similar combinations wherein ethanol is replaced by methanol, propanol, butanol, 2-propanol, 1,1-dimethylethanol, 2,2,2-trifluoroethanol, cyclopentanol or cyclohexanol.

When an alcohol compound of formula (d) is copresent during reaction according to the inventive method, it is desirable to use the alcohol compound in a proportion of 0.01 to 50 mol, more preferably 1 to 30 mol per mol of the ketone compound in order that an optically active alcohol be produced in high optical and chemical yields.

In the inventive method, a metal hydride is typically used as the hydride reagent. The metal hydride used herein is not critical. Typical examples include lithium aluminum hydride, lithium aluminum tri(t-butoxy)hydride, lithium boron hydride, sodium boron hydride, potassium boron hydride, calcium boron hydride, ammonium boron hydride, and sodium cyanoboron hydride.

Where metal trialkoxy boron hydride complexes such as sodium boron tri(methoxy)hydride, sodium boron tri (ethoxy)hydride, sodium boron tri(isopropoxy)hydride, sodium boron tri(t-butoxy)hydride, potassium boron tri (isopropoxy)hydride, and potassium boron tri(t-butoxy) hydride are used, optically active alcohols are obtained in high chemical and optical yields without the assistance of the alcohol compounds of formula (d).

In the practice of the invention, the reaction is preferably carried out in a liquid phase. A solvent may be then used if necessary. Useful examples of the solvent used herein include aliphatic hydrocarbon solvents, aromatic hydrocarbon solvents, alicyclic hydrocarbon solvents, ester solvents, ether solvents, and halide solvents. Preferred solvents are halide solvents such as carbon tetrachloride, chloroform, and Freon-113 and aromatic hydrocarbon solvents such as toluene. The amount of the solvent, if used, is generally 1 mL to 1 L per mmol of the ketone compound. Using about 5 to 100 ml of the solvent per mmol of the ketone compound is effective because optically active alcohols are obtained in high chemical and optical yields.

The reaction temperature is generally −100° C. to 50° C., preferably −80° C. to 30° C., more preferably −60° C. to 0° C. The reaction pressure is atmospheric insofar as the solvent does not volatilize.

The reaction time is generally about 1 minute to 10 days. The progress of reaction can be monitored by taking samples from the reaction mixture at intervals and analyzing them by thin layer chromatography (TLC), gas chromatography (GC) or the like.

The end optically active alcohol is recovered and purified from the resulting reaction mixture by well-known procedures, for example, by a proper combination of distillation, adsorption, extraction, recrystallization and other steps.

EXAMPLE

Examples of the present invention are given below by way of illustration and not by way of limitation.

Example 1

A reactor was charged with 0.55 mmol of sodium boron hydride. In an argon atmosphere, 2.0 ml of chloroform was added and 100 μl (1.7 mmol) of ethanol was then added. The contents were stirred for 30 minutes at room temperature. The reactor was cooled to −20° C. whereupon 1.5 ml of a chloroform solution containing 0.0125 mmol (2.5 mol %) of the optically active cobalt (II) complex of formula (a-7) was added dropwise. The mixture were stirred for 15 minutes at −20C whereupon 1.5 ml of a chloroform solution containing 0.5 mmol of 2,2-dimethylchromanone was slowly added dropwise. Stirring was continued at −20° C. Reaction completed in 3 days. A product was isolated and purified from the reaction mixture by silica gel column chromatography, obtaining a quantitative amount of 2,2-dimethylchromanol. The product was analyzed by high speed liquid chromatography (optically active column: CHIRALPACK AD by Dicell K.K.) to find an optical purity of 85% ee.

Examples 2–6

Reaction was carried out as in Example 1 except that metal hydrides as shown in Table 1 were used instead of the sodium boron hydride. Reaction completed in 2 to 6 days. In all Examples, 2,2-dimethylchromanol was quantitatively obtained. The products were analyzed for optical yield, which is shown in Table 1.

TABLE 1

|  | Hydride reagent | Optical yield (% ee) |
|---|---|---|
| Example 1 | $NaBH_4$ | 85 |
| Example 2 | $KBH_4$ | 87 |
| Example 3 | $LiBH_4$ | 52 |
| Example 4 | $Ca(BH_4)_2$ | 48 |
| Example 5 | $Me_4NBH_4$ | 39 |
| Example 6 | $Et_4NBH_4$ | 35 |

Example 7

Reaction was carried out as in Example 1 by using sodium boron tri(methoxy)hydride $NaBH(OMe)_3$ instead of the sodium boron hydride and without adding ethanol. Reaction completed in 4 days. 2,2-dimethylchromanol was quantitatively obtained. The product had an optical yield of 54% ee.

Examples 8–15

A reactor was charged with 0.75 mmol of sodium boron hydride. In an argon atmosphere, 5.0 ml of chloroform was added and 4.3 mmol of an alcohol as shown in Table 2 was added. The contents were stirred for 1 hour at room temperature. Then 2.0 ml of a chloroform solution containing 0.025 mmol (5.0 mol %) of the optically active cobalt (II) complex of formula (a-7) was added dropwise. The mixture was stirred for 15 minutes at room temperature and then cooled to −20° C. After stirring for a further 20 minutes, 2.0 ml of a chloroform solution containing 0.5 mmol of 2,2-dimethylchromanone was slowly added dropwise. The mixture was stirred for 6 days at −20° C. In all Examples, 2,2-dimethylchromanol was quantitatively obtained. The products were analyzed for optical yield, which is shown in Table 2.

TABLE 2

|  | Alcohol | Optical yield (% ee) |
|---|---|---|
| Example 8 | methanol | 61 |
| Example 9 | ethanol | 88 |
| Example 10 | n-butanol | 74 |
| Example 11 | isopropyl alcohol | 69 |
| Example 12 | 2-methyl-2-propanol | 75 |
| Example 13 | cyclopentanol | 82 |
| Example 14 | cyclohexanol | 66 |
| Example 15 | ethylene glycol | 59 |

Examples 16–23

Reaction was carried out as in Example 9 except that solvents as shown in Table 3 were used instead of the chloroform. Reaction completed in 2 to 6 days. In all Examples, 2,2-dimethylchromanol was quantitatively obtained. The products were analyzed for optical yield, which is shown in Table 3.

TABLE 3

|  | Solvent | Optical yield (% ee) |
|---|---|---|
| Example 9 | chloroform | 88 |
| Example 16 | dichloromethane | 57 |
| Example 17 | carbon tetrachloride | 80 |
| Example 18 | 1,2-dichloroethane | 44 |
| Example 19 | toluene | 65 |
| Example 20 | tetrahydrofuran | 23 |
| Example 21 | diethyl ether | 60 |
| Example 22 | ethylacetate | 45 |
| Example 23 | Freon 113 | 64 |

Examples 24–27

Reaction was carried out as in Example 9 except that optically active cobalt (II) complexes as shown in Table 4 were used instead of the optically active cobalt (II) complex of formula (a-7). Reaction completed in 3 to 6 days. In all Examples, 2,2-dimethylchromanol was quantitatively obtained. The products were analyzed for optical yield, which is shown in Table 4.

TABLE 4

| Example | Cobalt(II)complex | Chemical yield (%) | Optical yield (% ee) |
|---------|-------------------|--------------------|-----------------------|
| 9 | | quant. | 88 |
| 24 | | quant. | 51 |
| 25 | | quant. | 51 |
| 26 | | quant. | 83 |
| 27 | | quant. | 92 |

Examples 28–45

Reaction was carried out as in Example 9 except that ketones as shown in Table 5 were used instead of the 2,2-dimethylchromanone. Crude products were processed by silica gel column chromatography for isolation and purification. The optically active alcohols were analyzed for optical yield, which is shown in Table 5.

TABLE 5

| Example | Ketone | Optical yield (% ee) |
|---|---|---|
| 9 | 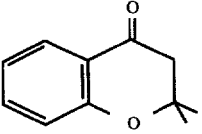 | 88 |
| 28 | 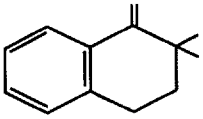 | 90 |
| 29 | 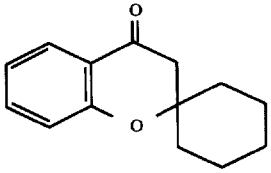 | 80 |
| 30 | 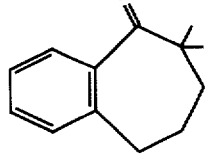 | 80 |
| 31 | 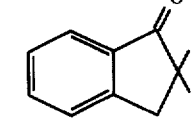 | 76 |
| 32 | 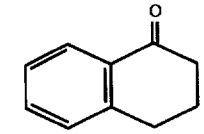 | 64 |
| 33 | 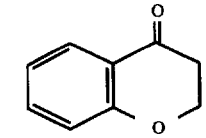 | 60 |
| 34 | 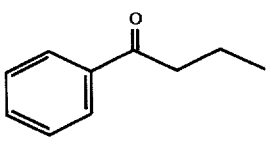 | 50 |
| 35 | 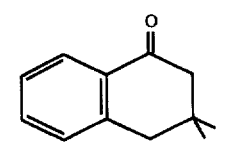 | 47 |
| 36 | 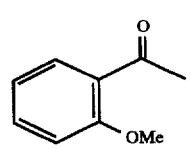 | 47 |

TABLE 5-continued

| Example | Ketone | Optical yield (% ee) |
|---|---|---|
| 37 | 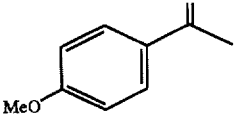 | 47 |
| 38 | 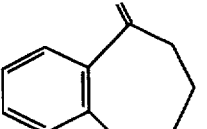 | 43 |
| 39 | 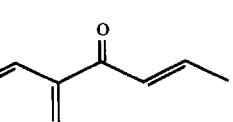 | 42 |
| 40 |  | 47 |
| 41 | 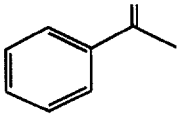 | 29 |
| 42 | 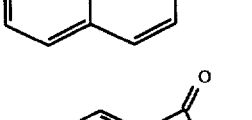 | 27 |
| 3 | 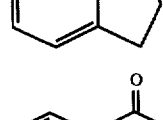 | 21 |
| 44 | 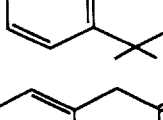 | 26 |

Example 46

A reactor was charged with 0.75 mmol of sodium boron hydride. In an argon atmosphere, 5.0 ml of chloroform was added and 1 ml of ethanol and 1 ml of tetrahydrofurfuryl alcohol were then added. The contents were stirred for 30 minutes at room temperature. The reactor was cooled to −20° C. whereupon 2 ml of a chloroform solution containing 0.025 mrnol (5 mol %) of the optically active cobalt (II) complex of formula (a-9) was added dropwise. The mixture were stirred for 15 minutes at −20° C. whereupon 2 ml of a chloroform solution containing 0.5 mmol of 6-methoxytetralone was slowly added dropwise. Stirring was continued at −20° C. Reaction completed in 3 days. A product was isolated and purified from the reaction mixture by silica gel column chromatography, obtaining a quantitative amount of 6-methoxytetralol. The product was analyzed by high speed liquid chromatography (optically active column: CHIRALPACK AD by Dicell K.K.) to find an optical yield of 91% ee.

Examples 47–52

Reaction was carried out as in Example 46 except that alcohol compounds as shown in Table 6 were used instead of the tetrahydrofurfuryl alcohol. Reaction completed in ½ to 6 days. In all Examples, 6-methoxytetralol was quantitatively obtained. The products were analyzed for optical yield, which is shown in Table 6.

TABLE 6

| | Alcohol | Optical yield (% ee) |
|---|---|---|
| Example 47 | ethylene glycol monomethyl ether | 75 |
| Example 48 | ethylene glycol monoethyl ether | 73 |
| Example 49 | tetrahydropyrane-2-methanol | 86 |
| Example 50 | tetrahydro-3-furan-methanol | 70 |
| Example 51 | 5-methyltetrahydrofuran-2-methanol | 84 |
| Example 52 | furfuryl alcohol | 91 |

Examples 53–57

Reaction was carried out as in Example 46 except that compounds as shown in Table 7 were used instead of the ethanol. Reaction completed in ½ to 6 days. In all Examples, 6-methoxytetralol was quantitatively obtained. The products were analyzed for optical yield, which is shown in Table 7.

TABLE 7

| | Alcohol | Optical yield (% ee) |
|---|---|---|
| Example 53 | methanol | 91 |
| Example 54 | 2-propanol | 90 |
| Example 55 | 1,1-dimethylethanol | 86 |
| Example 56 | cyclopentanol | 88 |
| Example 57 | 2,2,2-trifluoroethanol | 91 |

Example 58

In an argon atmosphere, a first reactor was charged with 5.0 ml of a chloroform suspension containing 29 mg (0.75 mmol) of sodium boron hydride. Then 30 μl of methanol and 1 ml of tetrahydrofurfuryl alcohol were added thereto. The first mixture was stirred for 3.0 hours at 0° C. In an argon atmosphere, a second reactor was charged with 2.0 ml of a 1 mol % chloroform solution containing 0.005 mmol of the optically active cobalt (II) complex of formula (a-10). Then 30 μl of methanol and 2.0 ml of a chloroform solution containing 105 mg (0.5 mmol) of 2,3,4,5,6-pentafluorobenzophenone were added thereto. The second mixture was cooled to 0° C. and stirred for 10 minutes. Thereafter, the first mixture prepared in the first reactor was slowly added dropwise to the second reactor. Stirring was continued at 0° C. for reaction to take place. Reaction completed in 15 minutes. Upon isolation and purification from the reaction mixture by silica gel column chromatography, an optically active alcohol was quantitatively obtained. The product was analyzed by high speed liquid chromatography (optically active column: CHIRALPACK AD by Dicell K.K.) to find an optical yield of 85% ee.

Examples 59–65

Reaction was carried out as in Example 58 except that ketones as shown in Table 8 were used instead of the 2, 3, 4, 5, 6-pentafluorobenzophenone. Reaction completed in ¼ to 3 hours. In all Examples, optically active alcohols were quantitatively obtained. The products were analyzed for optical yield, which is shown in Table 8.

TABLE 8

| Example | Ketone compound | Optical yield (% ee) |
|---|---|---|
| 59 | (tetralone structure) | 54 |
| 60 | (cyclohexyl propyl ketone) | 97 |
| 61 | (phenyl cyclohexyl ketone) | 95 |
| 62 | (phenyl cyclopropyl ketone) | 90 |
| 63 | (methyl benzoylacetate, PhCOCH₂COOCH₃) | 85 |
| 64 | (dibenzoylmethane, PhCOCH₂COPh) | 96 |
| 65 | (phenylpropynyl methyl ketone) | 30 |

Example 66

Preparation of optically active cobalt (III) complex

In 5 ml of dichloroethane, was dissolved 697 mg (1 mmol) of the optically active cobalt (II) complex of formula (a-10). 127mg (0.5 mmol) of iodine was added to the solution, which was stirred for 2 hours in a nitrogen atmosphere and at room temperature. After the completion of reaction, the solvent was distilled off in vacuum, obtaining an optically active cobalt (III) complex of formula (a-18). This complex was examined for structure by X-ray diffractometry, on the basis of analysis of the X-ray diffraction data, the optically active cobalt (III) complex was regarded to have a steric structure as shown in FIG. 1.

Preparation of optically active alcohol

In an argon atmosphere, a first reactor was charged with 5.0 ml of a chloroform suspension containing 29 mg (0.75 mmol) of sodium boron hydri-de. Then 30 μl of methanol and 1 ml of tetrahydrofurfuryl alcohol were added thereto. The first mixture was stirred for 3.0 hours at 0° C. In an argon atmosphere, a second reactor was charged with 2.0 ml of a 1 mol % chloroform solution containing 0.005 ni.mol of the optically active cobalt (III) complex of formula (a-18). Then 30 μl of methanol and 2.0 ml of a chloroform solution containing 80 mg (0.5 mmol) of tetralone were added thereto. The second mixture was cooled to 0° C. and stirred for 10 minutes. Thereafter, the first mixture prepared in the first reactor was slowly added dropwise to the second reactor. Stirring was continued at 0° C. for reaction to take place. Reaction completed in 15 minutes. Upon isolation and purification from the reaction mixture by silica gel column chromatography, an optically active alcohol was quantitatively obtained. The product was analyzed by high speed liquid chromatography (optically active column: CHIRAL-PACK AD by Dicell K.K.) to find an optical yield of 92% ee.

Example 67

Preparation of optically active cobalt (II) complex

Synthesis of ligand

In 70 ml of ethanol was dissolved 1.06 g (5 mmol) of (S.S)-1,2-diphenylethylenediamine. In a nitrogen atmosphere and at room temperature, 30 ml of an ethanol solution containing 2.32 g (10.5 mmol) of 2-formyl-(2,4,6-trimethylphenyl)-1,3-dioxobutane was added to the solution, which was stirred for 2 hours at room temperature. The reaction mixture was then heated to 50° C. and reaction took place in 2 hours. After the completion of reaction, the solvent was distilled off in vacuum, obtaining a crude product. The crude product was dissolved in dichloromethane/ether/hexane for recrystallization, obtaining 2.28 g (isolation yield 71%) of an optically active ligand (N,N'-bis[3-oxo-2-(2,4,6-trimethylbenzoyl)butylidene]-(1S, 2S)-1,2-diphenylethylenediamine) as white crystals. The thus obtained optically active ligand was analyzed by $^1$H-NMR, IR, and elemental analysis and measured for melting point and specific rotatory power. The results are shown below.

$^1$H-NMR (CDCl$_3$): d=1.92 (6H, s), 1.97 (6H, s), 2.26 (6H, s), 2.62 (6H, br), 4.41 (2H, d, J=8.2 Hz), 6.70–7.25 (16H, m)

IR (KBr): 3028, 2968, 2916, 2856, 1614, 1589, 1454, 1404, 1352, 1299, 1251 cm$^{-1}$

Elemental analysis (for C$_{42}$H$_{44}$N$_2$O$_4$): Found: C 78.72%, H 6.92%, N 4.37% Calcd. C 77.76%, H 6.85%, N 4.27%

Melting point: 206°–210° C.

Specific rotatory power $[\alpha]_D^{28}$ : +72.3° cpb 0.507, CHCl$_3$)

Synthesis of cobalt (II) complex

To 6.4 g (10 mmol) of the optically active ligand prepared above was added 180 ml of methanol. In a nitrogen stream, the mixture was stirred until a solution was obtained. After 30 minutes of stirring, 10 ml of an aqueous solution containing 0.88 g (22 mmol) of sodium hydroxide was added to the solution, which was stirred at 50° C. After 30 minutes, 14 ml of an aqueous solution containing 2.6 g (11 mmol) of cobalt chloride hexahydrate was added dropwise whereupon an orange precipitate settled out. The precipitate was cooled to room temperature and 100 ml of water was added thereto to form a reaction suspension. In a nitrogen atmosphere, the reaction suspension was filtered and the residue was washed with 120 ml of water. The residue was dried in a nitrogen stream, taken out in a nitrogen box, and vacuum dried at 120° C. for 2 hours, obtaining 6.5 g (yield 93%) of an orange cobalt (II) complex of formula (a-7). The thus obtained cobalt (II) complex was measured for melting point and analyzed by EIMS and IR. The results are shown below.

Melting point: 292°–296° C. (DSC: 293°–299° C.) EIMS: Found 697.2474 Calcd. (for C$_{42}$H$_{42}$N$_2$O$_4$Co) 697.2477

IR (KBr): 3050, 3010, 2990, 2900, 1640, 1560, 1470, 1400, 1340, 1280, 1260, 1025, 1020, 990, 880, 840, 760, 740, 700, 595, 540 cm$^{-1}$

Examples 68–75

As in Example 67, optically active ligands were prepared using 1,3-diketone compounds and 1,2-diphenylamine compounds as shown in Table 9, and then optically active cobalt (II) complexes were prepared therefrom. There were obtained optically active cobalt (II) complexes of formulae (a-3), (a-7) to (a-12). The optically active cobalt (II) complexes were measured for melting point. The optically active cobalt (II) complexes of formula (a-9) and (a-10) were further analyzed by mass analysis (EIMS). The results are shown in Table 9.

TABLE 9-1

| Example | 1,3-diketone compound | 1,2-diphenyldiamine compound | Optically active cobalt(II) complex | |
|---|---|---|---|---|
| 68 | ![structure] | ![structure] | ![structure] mp: 285° C. | (a-2) |

TABLE 9-1-continued

| Example | 1,3-diketone compound | 1,2-diphenyldiamine compound | Optically active cobalt(II) complex | |
|---|---|---|---|---|
| 69 | | | | (a-3) |
| | | | mp: 170° C. | |
| 70 | | | | (a-7) |
| | | | mp: 293° C. | |
| 71 | | | | (a-8) |
| | | | mp: 302° C. | |
| 72 | | | | (a-9) |
| | | | mp: 285° C. | |

TABLE 9-1-continued

| Example | 1,3-diketone compound | 1,2-diphenyldiamine compound | Optically active cobalt(II) complex | |
|---|---|---|---|---|
| 73 | | | | (a-10) mp: 170° C. |
| 74 | | | | (a-11) mp: 293° C. |
| 75 | | | | (a-12) mp: 302 C. |

There has been described a method for preparing optically active alcohols from ketones using easy-to-handle hydride reagents as typified by sodium borohydride as a reducing agent. The optically active alcohols are useful as intermediates for the synthesis of physiologically active compounds such as drugs and pesticides, functional materials such as liquid crystals, and raw materials for synthesis in fine chemistry. Novel optically active cobalt (II) complexes are useful as a catalyst in the preparation of optically active alcohols.

We claim:

1. A method for preparing an optically active alcohol comprising the step of reacting a ketone compound with a hydride reagent in the presence of an optically active metal compound, wherein the optically active metal compound is a cobalt (II) complex of the following general formula (a):

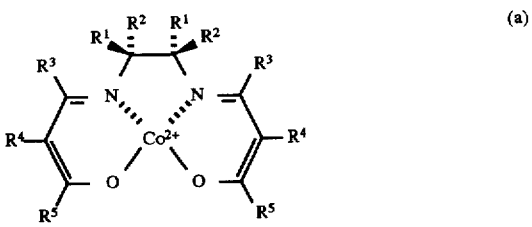

(a)

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent.

2. The method of claim 1 wherein said optically active cobalt (II) complex is used in an amount of 0.001 to 50 mol % per mol of the ketone compound.

3. The method of claim 1 wherein said ketone compound is of the following general formula (b):

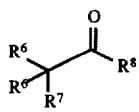
(b)

wherein $R^6$, $R^7$, and $R^8$ may be the same or different, and are independently selected from the group consisting of a normal or branched alkyl group, cycloalkyl group, and aromatic group, which may have a substituent, or the two $R^6$ groups or $R^7$ and $R^8$, taken together, may form a ring.

4. The method of claim 1 wherein said hydride reagent is a metal hydride.

5. The method of claim 3 wherein said ketone compound is an acetophenone derivative of the following formula (b-1), an α-tetralone derivative of the following formula (b-2) or a chromanone of the following formula (b-3):

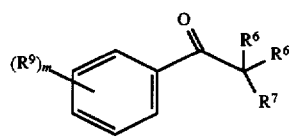
(b-1)

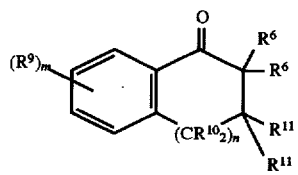
(b-2)

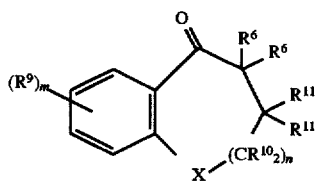
(b-3)

wherein $R^6$ and $R^7$ may be the same or different, and are as defined in formula (b), $R^9$, $R^{10}$, and $R^{11}$ are independently selected from the group consisting of a hydrogen atom, halogen atom, normal or branched alkyl, cycloalkyl, aryl, nitro, cyano, alkoxy, acyl, alkoxycarbonyl, amino, and silyl group, which may have a substituent, letter n is equal to 0 or 1, m is an integer of 1 to 4, when m is an integer of 2 to 4, a corresponding plurality of $R^9$ groups may be the same or different, or the $R^{10}$ groups or $R^{11}$ groups, taken together, may form a ring, X is a hetero-atom, whereby there is obtained an optically active alcohol of the following general formula (c-1), (c-2) or (c-3):

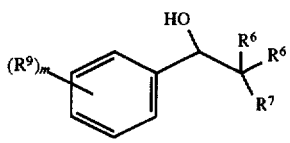
(c-1)

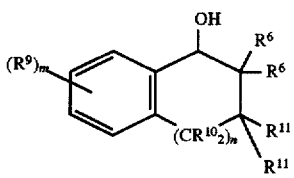
(c-2)

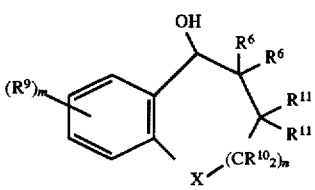
(c-3)

wherein $R^6$ to $R^{11}$, n and m are as defined above.

6. The method of claims 1 or 2 to 5 wherein the reaction is carried out in the co-presence of an alcohol compound.

7. The method of claim 6 wherein said alcohol compound is of the following formula (d):

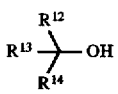
(d)

wherein $R^{12}$, $R^{13}$, and $R^{14}$ may be the same or different, and are independently selected from the group consisting of a hydrogen atom, normal or branched alkyl group, cycloalkyl group, aryl group, and normal or branched ether group containing a hetero-atom, which may have a substituent, or $R^{12}$ and $R^{13}$, taken together, may form a ring.

8. The method of claim 7 wherein said alcohol compound is used alone or a mixture of said alcohol compounds is used.

9. The method of claim 5 wherein said alcohol compound is used in an amount of 0.01 to 50 mol per mol of said ketone compound.

10. An optically active cobalt (II) complex of the following general formula (a):

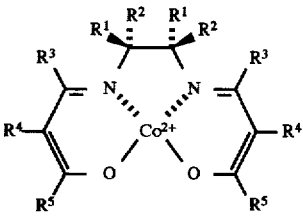
(a)

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent.

11. A method for preparing an optically active alcohol comprising the step of reacting a ketone compound of the formula (b)

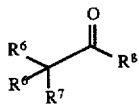

wherein $R^6$, $R^7$, and $R^8$ may be the same or different, and are independently selected from the group consisting of a normal or branched alkyl group, cycloalkyl group, and aromatic group, which may have a substituent, or the two $R^6$ groups or $R^7$ and $R^8$, taken together, may form a ring with a metal hydride compound in the presence of an optically active metal compound, wherein the optically active metal compound is a cobalt (II) complex of the following general formula (a):

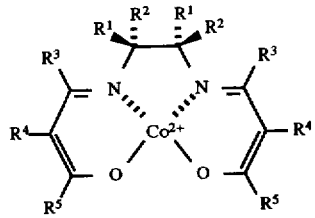

(a)

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent, wherein the optically active cobalt (II) complex is used in an amount of 0.001 to 50 mol % per mol of the ketone compound and optically active alcohols corresponding to said ketone compound are obtained.

12. The method of claim 11 wherein said ketone compound is a member selected from the group consisting of acetophenones, a- tetralones and chromanones.

13. The method of claim 11 wherein the optically active cobalt (II) metal complex is a member selected from the group consisting of at least one of the following compounds:

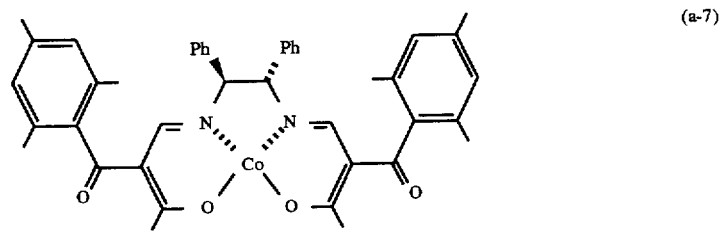

(a-7)

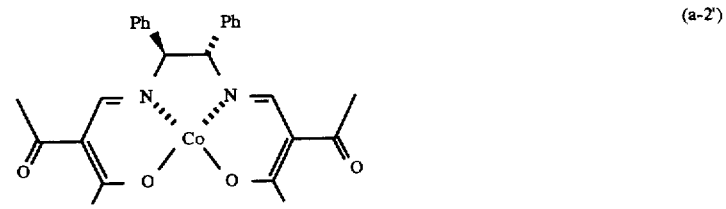

(a-2')

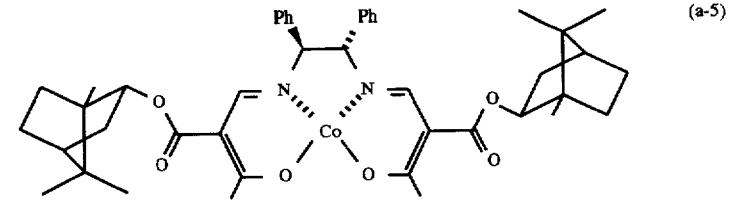

(a-5)

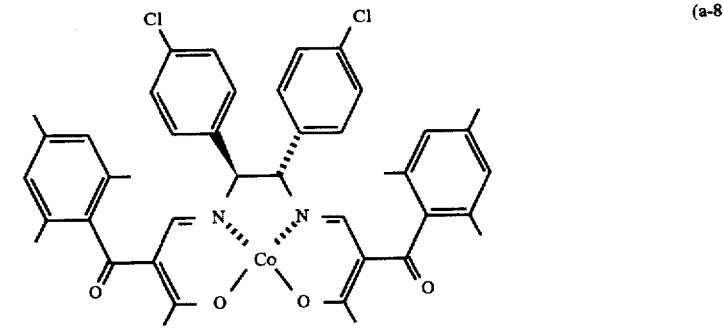

(a-8)

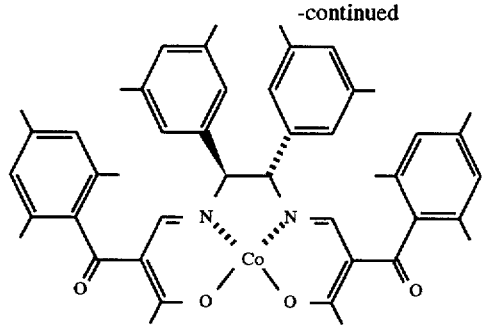
(a-10)'
14. The optically active cobalt II complex of claim 10 wherein the optically active cobalt (II) metal complex is a member selected from the group consisting of at least one of the following compounds:
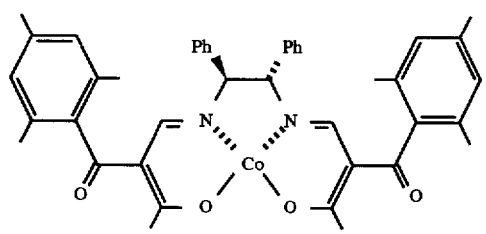
(a-7)
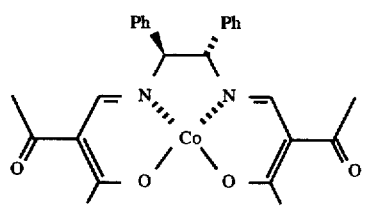
(a-2')
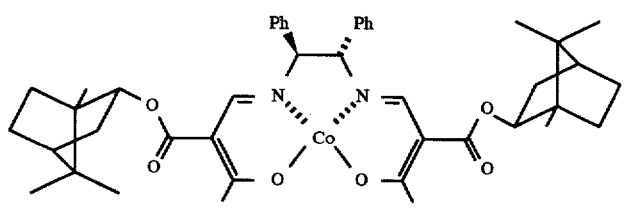
(a-5)
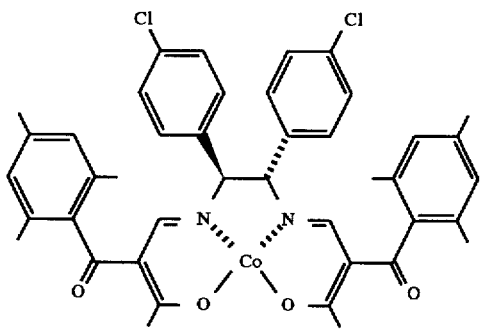
(a-8)

-continued (a-10)'

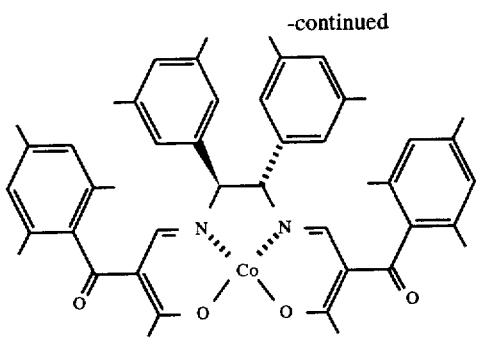

15. A method for preparing an optically active alcohol comprising the step of reacting a ketone compound with a hydride reagent in the presence of an optically active metal compound, wherein the optically active metal compound is a metal complex of the following general formula (a'):

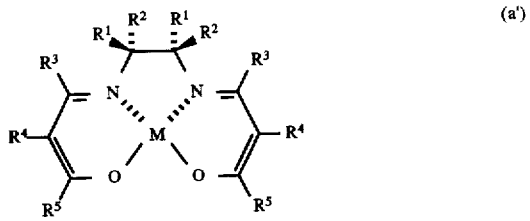

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent, and wherein M in the optically active metal compound is at least one transition metal selected from the group consisting of titanium, vanadium, manganese, iron, cobalt, zinc, nickel, ruthenium, rhodium, hafnium, and zirconium.

16. The method of claim 15 wherein said optically active metal compound is selected from the group consisting of an optically active titanium (IV) complex, optically active iron (III) complex, optically active ruthenium (III) complex, optically active oxovanadium (IV) complex, optically active manganese (III) complex, and optically active cobalt (III) complex, and optically active cobalt (II) complex.

17. The method of claim 15 wherein said optically active metal compound is a complex of at least one transition metal selected from the group consisting of iron, nickel, titanium and ruthenium and optically active cobalt (II) complex.

18. The method of claim 15 wherein said optically active metal complex is used in an amount of 0.001 to 50 mol % per mol of the ketone compound.

19. The method of claim 15 wherein said ketone compound is of the following general formula (b):

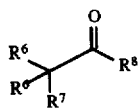

(b)

wherein $R^6$, $R^7$, and $R^8$ may be the same or different, and independently selected from the group consisting of a normal or branched alkyl group, cycloalkyl group, and aromatic group, which may have a substituent, or the two $R^6$ groups or $R^7$ and $R^8$, taken together, may form a ring.

20. The method of claim 15, wherein said hydride reagent is a metal hydride.

21. The method of any one of claims 15 to 20, wherein reaction is carried out in the co-presence of an alcohol compound.

22. The method of claim 19 wherein said alcohol compound is used in an amount of 0.01 to 50 mol per mol of said ketone compound.

23. An optically active metal complex of the following general formula (a'):

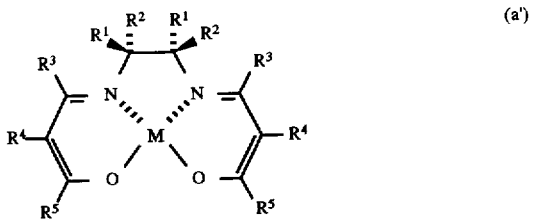

wherein each of $R^1$ and $R^2$ which are different, is a hydrogen atom, normal or branched alkyl group or aryl group, which may have a substituent, or two $R^1$ groups or two R2 groups, taken together, may form a ring, and R3, $R^4$ and $R^5$ may be the same or different, and are independently selected from the group consisting of a hydrogen atom, normal or branched alkyl group, aryl group, acyl group, and alkoxycarbonyl group, which may have a substituent, and wherein M in the optically active metal compound is at least one transition metal selected from the group consisting of titanium, vanadium, manganese, iron, cobalt, zinc, ruthenium, rhodium, hafnium, and zirconium.

24. The optically active metal complex of claim 23 wherein the optically active metal compound is a complex of at least one transition metal selected from the group consisting of iron, nickel, titanium and ruthenium and optically active cobalt (II) complex.

25. A method for preparing an optically active alcohol comprising the step of reacting a ketone compound of the formula (b)

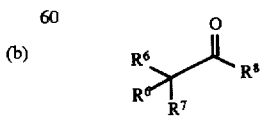

(b)

wherein $R^6$, $R^7$, and $R^8$ may be the same or different, and are independently selected from the group consisting of a normal or branched alkyl group, cycloalkyl group, and aromatic group, which may have a substituent, or the two R6 groups or $R^7$ and $R^8$, taken together, may form a ring with a metal hydride compound in the presence of an optically active metal compound, wherein the optically active metal compound is a metal complex of the following general formula (a'):

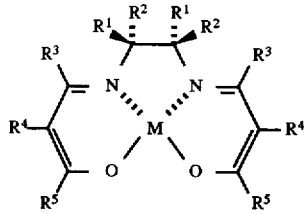
(a')

wherein each of $R^1$ and $R^2$, which are different, is a hydrogen atom, normal or branched alkyl group or aryl group, which may have a substituent, or two $R^1$ groups or two $R^2$ groups, taken together, may form a ring, and $R^3$, $R^4$ and $R^5$ may be the same or different, and are independently selected from the group consisting of a hydrogen atom, normal or branched alkyl group, aryl group, acyl group, and alkoxycarbonyl group, which may have a substituent, wherein the optically active metal complex is used in an amount of 0.001 to 50 mol % per mol of the ketone compound and optically active alcohols corresponding to said ketone compound are obtained, and wherein M in the optically active metal compound is at least one transition metal selected from the group consisting of titanium, vanadium, manganese, iron, cobalt, zinc, ruthenium, rhodium, hafnium, and zirconium.

26. The method of claim 25 wherein the optically active metal compound is a complex of at least one transition metal selected from the group consisting of iron and nickel, titanium and ruthenium and optically active cobalt II complex.

27. The method of claim 25 wherein said ketone compound is a member selected from the group consisting of acetophenones, α-tetralones and chromanones.

* * * * *